US008679838B2

(12) United States Patent
Suzuki et al.

(10) Patent No.: US 8,679,838 B2
(45) Date of Patent: Mar. 25, 2014

(54) HUMAN SERUM FOR CELL CULTURE

(75) Inventors: Koji Suzuki, Hiroshima (JP); Seishin Tanaka, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 209 days.

(21) Appl. No.: 12/705,298

(22) Filed: Feb. 12, 2010

(65) Prior Publication Data

US 2010/0167402 A1 Jul. 1, 2010

Related U.S. Application Data

(62) Division of application No. 11/719,392, filed as application No. PCT/JP2005/020238 on Nov. 2, 2005, now abandoned.

(30) Foreign Application Priority Data

Nov. 19, 2004 (JP) ................. 2004-335344

(51) Int. Cl.
| | | |
|---|---|---|
| *C12N 5/07* | (2010.01) | |
| *C12N 5/10* | (2006.01) | |
| *A01N 1/02* | (2006.01) | |
| *C12N 5/00* | (2006.01) | |
| *C12N 5/02* | (2006.01) | |
| *C12N 5/071* | (2010.01) | |
| *C12M 1/00* | (2006.01) | |
| *C12M 1/38* | (2006.01) | |
| *C12M 3/00* | (2006.01) | |
| *C12M 1/34* | (2006.01) | |

(52) U.S. Cl.
USPC ............ 435/355; 435/2; 435/325; 435/408; 435/392; 435/372; 435/283.1; 435/286.4; 435/286.7; 435/288.1; 435/288.4; 435/288.5

(58) Field of Classification Search
None
See application file for complete search history.

(56) References Cited

U.S. PATENT DOCUMENTS

| | | | |
|---|---|---|---|
| 4,189,382 A * | 2/1980 | Zine, Jr. ..................... 210/714 |
| 4,807,676 A | 2/1989 | Cerny et al. | |
| 4,837,047 A * | 6/1989 | Sato et al. ..................... 422/41 |
| 5,578,027 A * | 11/1996 | Drago et al. ................. 604/408 |
| 2006/0178610 A1 * | 8/2006 | Nowakowski ............. 604/4.01 |

FOREIGN PATENT DOCUMENTS

| | | |
|---|---|---|
| EP | 1464697 A1 | 10/2004 |
| JP | S57-197471 | 12/1982 |
| JP | S62-502594 | 10/1987 |
| JP | 04-083165 | 3/1992 |
| JP | H04-083167 | 3/1992 |
| JP | H06-227993 | 8/1994 |
| JP | H07-330620 | 12/1995 |
| JP | 2000-000228 | 1/2000 |
| JP | 2001-275662 | 10/2001 |
| JP | 2004-269409 | 9/2004 |
| JP | 2005-329222 | 12/2005 |
| JP | 2006-010416 | 1/2006 |
| WO | WO-00/27996 | 5/2000 |
| WO | WO-2004/103440 | 2/2004 |

OTHER PUBLICATIONS

McAlinden et al., "Comparison of Cancellous Bone-Derived Cell Proliferation in Autologous Human and Fetal Bovine Serum," Cell Transplantation, vol. 9, 2000, pp. 445-451.

Stute et al., "Autologous serum for isolation and expansion of human mesenchymal stem cells for clinical use," Experimental Hematology, 32, 2004, pp. 1212-1235.

Mizuno et al., "Human autologous serum obtained using a completely closed bag system as a substitute for foetal calf serum in human mesenchymal stem cell cultures," Cell Biology International, 30, 2006., pp. 521-524.

Notice of Reasons for Rejection,from the Japan Patent Office, issued to JP Application No. 2006-544866, mailed Apr. 13, 2010, Not translated.

Meijer, et al., "The production of anti-inflammatory cytokines in whole blood by physico-chemical induction", Inflammation Research 52 (2003), pp. 404-407.

* cited by examiner

*Primary Examiner* — Vanessa L. Ford
*Assistant Examiner* — Lakia Tongue
(74) *Attorney, Agent, or Firm* — Muncy, Geissler, Olds & Lowe, P.C.

(57) ABSTRACT

It is intended to provide a serum which contains a large amount of growth factors capable of efficiently promoting the growth of stem cells. A human serum for cell culture which shows a residual ratio of platelets remaining within 20 minutes after blood collection in relation to the whole amount of the platelets is 0% to 20%, and a release ratio of cell growth factors is 20% to 100%.

5 Claims, 5 Drawing Sheets

HUMAN SERUM FOR CELL CULTURE

CROSS REFERENCE TO RELATED APPLICATIONS

This application is a Divisional of application Ser. No. 11/719,392, filed on May 15, 2007, now abandoned which is a U.S. National Stage of International Application No. PCT/JP2005/020238 filed on Nov. 2, 2005, which claims priority of Japan Application No. 2004-335344 filed on Nov. 19, 2004, for which priority is claimed under 35 U.S.C. §120 and 35 U.S.C. §119.

TECHNICAL FIELD

The present invention relates to a human serum for cell culture, and more particularly to a human serum for cell culture including a large amount of cell growth factors.

This application is based upon and claims priority from Japanese Patent Application No. 2004-335344, filed on Nov. 19, 2004, the entire contents of which are incorporated herein by reference.

BACKGROUND ART

Currently, in the field of regenerative medicine, studies in which stem cells collected from a subject are caused to proliferate or differentiate ex vivo, and are thereafter transplanted into a subject, thereby promoting regeneration of tissue of the subject, have been carried out. Stem cells are multipotent and can differentiate into a variety of tissues and organs, and they have been attracting attention as cells which are the key to regenerative medicine.

It has been known that in ex vivo cultural proliferation of stem cells, the addition of a serum to the medium is effective. However, when human therapies are targeted, the use of a serum derived from an animal other than humans should be avoided in light of possible safety problems. Therefore, the use of a serum prepared from blood collected from a human, in particular, collected from the same subject is desired. In addition, a culture of stem cells in the field of regenerative medicine requires relatively larger amounts of serum in comparison with blood tests.

As a method of preparing such a serum, a method in which a blood collection tube is used that contains a blood coagulation accelerating solid, such as glass powder, is disclosed (see Patent Document 1). Furthermore, a method of facilitating collection of a serum having a large amount and many kinds of growth factors by bringing the blood into contact with glass powder so as to rapidly separate a coagulation substance such as fibrin mixed in the serum is disclosed (see Patent Document 2). Moreover, a method of producing a serum as a raw material with human plasma is disclosed (see Patent Document 3). In addition, a method of obtaining growth factors by adding a calcium compound and glass beads to plasma is disclosed (see patent document 4).

Patent Document 1: Japanese Unexamined Patent Application Publication No. 2000-000228
Patent Document 2: Japanese Unexamined Patent Application Publication No. Hei 04-83165
Patent Document 3: Japanese Unexamined Patent Application Publication No. 2001-275662
Patent Document 4: Japanese Unexamined Patent Application Publication No. 2004-269409

DISCLOSURE OF THE INVENTION

Problems to be Solved by the Invention

The method disclosed in patent document 1 or 2, however, uses a low capacity blood collection tube designed for blood tests, and therefore, preparatory procedures must be repeated many times to prepare a serum in an amount required for a culture of stem cells. Hence, this method is not suited for practical applications. Furthermore, the method disclosed in patent document 3 uses thrombin as an anticoagulant, and therefore, is not desirable because it entails the infection risk caused by a substance of biologic origin. Moreover, the method disclosed in patent document 4 cannot efficiently culture stem cells because it uses plasma having only a small amount of cell growth factors as a raw material, and accordingly, the resulting serum does not contain sufficient cell growth factors.

The present invention was made in view of the foregoing problems, and it is an object of the present invention to provide a serum which contains a large amount of a growth factor capable of efficiently promoting the growth of stem cells.

Means for Solving the Problems

More specifically, the following is provided.

In a first aspect of the present invention, a human serum for cell culture obtained from a fluid comprising humoral components derived from blood having blood coagulation factors and platelets, and wherein a residual ratio of the platelets remaining within 20 minutes after blood collection in relation to the whole amount of the platelets is 0% to 20%, and a release ratio of cell growth factors is 20% to 100%.

According to the first aspect of the present invention, the release of the cell growth factors can be quickly promoted, resulting from the residual ratio of the platelets remaining within 20 minutes after collection of the blood in relation to the whole amount of the platelets is 0% to 20%. Furthermore, stem cells can be efficiently proliferated, resulting from the release ratio of cell growth factors being 20% to 100%. In addition, since the fluid including at least humoral components and platelets derived from blood is used, a serum having a larger amount of growth factors can be produced in comparison with the case where the serum is prepared from the plasma, thereby enabling the production of a serum having a cell growth effect equivalent to a fetal bovine serum.

The term "blood" used herein indicates whole blood including hemocytes (erythrocytes, leucocytes, platelets) and plasma (serum) as a liquid component, and a liquid containing at least one of these (for example, blood collected by apheresis). Furthermore, the term "serum" used herein means a pale yellow liquid obtained by allowing collected blood to stand, resulting in a reduction in fluidity, followed by separation from the red coagulated block (clot). The meaning of "serum" according to the present invention is different from common serums in terms of the production process not including separation from the clot, but it means a humoral component in the blood that is useful in cell culture and that includes coagulation factors and growth factors substantially equivalent to those in common serums. The term "humoral component derived from blood" used herein indicates "blood components other than hemocytes" or "mixture of blood components other than hemocytes and an agent such as an anticoagulant added thereto". The term "cell growth factor" used herein means a platelet-derived growth factor (PDGF), a transforming growth factor (TGF-β1), a vascular endothelial growth factor (VEGF), an insulin-like growth factor (IGF), a hepatocellular growth factor (HGF), a brain-derived neurotrophic factor (BDNF), a basic fibroblast growth factor (bFGF), or the like.

In addition, the term "release ratio of cell growth factors" used herein indicates a ratio of an amount of cell growth factors to a potential amount, where the amount of cell growth factors contained in a serum prepared from a predetermined amount of blood collected in a vacuum collection tube is assumed to be the potential amount (100% of cell growth factors are released).

In a second aspect of the present invention, a human serum for cell culture obtained from a fluid comprising humoral components derived from blood having blood coagulation factors and platelets, and wherein a content of the cell growth factors is greater than that of a human serum prepared from plasma.

According to the second aspect of the present invention, stem cells can be efficiently proliferated, due to the content of the cell growth factors of the human serum being greater than that of a human serum which is prepared from plasma. The term "plasma" used herein indicates a supernatant liquid obtained by adding an anticoagulant, such as heparin, CPD, or the like, to the collected blood, followed by centrifugal separation. The term "human serum prepared from plasma" used herein indicates a human serum obtained by centrifuging blood collected from the subject under conditions where the platelets are completely precipitated (for example, 4,400 (g)×5 (min.) or greater) to prepare plasma, followed by separating coagulation factors from the plasma.

In a third aspect of the present invention, a human serum for cell culture obtained from a fluid comprising humoral components derived from blood having blood coagulation factors and platelets, and wherein a content of the cell growth factors is greater than that of a human serum prepared by allowing the blood to coagulate.

According to the third aspect of the present invention, stem cells can be efficiently proliferated, due to the content of the cell growth factors of the human serum being greater than that of a human serum prepared by allowing the blood to coagulate. The term "human serum prepared by allowing the blood to coagulate" used herein indicates letting human serum obtained from blood collected from the subject coagulate in a flexible vessel at room temperature for approximately one hour, followed by centrifugal separation.

In a fourth aspect of the present invention, the human serum for cell culture according to any one of the first to third aspects, the cell growth factors comprise at least one of PDGF-BB and TGF-β1.

According to the fourth aspect of the present invention, stem cells can be efficiently proliferated, due to the cell growth factors comprising at least one of PDGF-BB and TGF-β1, which are higher among the growth factors in terms of cellular proliferative potential. Here, PDGF-BB indicates one of three types of PDGF (dimer) (PDGF-AA,PDGF-BB, PDGF-AB).

In a fifth aspect of the present invention, the human serum for cell culture according to any one of the first to fourth aspects, the cell growth factors are obtained by bringing the fluid into contact with a processed glass body.

In order to activate the platelets in the fluid to have the cell growth factors released, the fluid is required to be brought into contact with foreign matter. In the human serum for cell culture according to the fifth aspect of the present invention, cell growth factors can be more efficiently released in comparison with the case of a polyethylene pellet, as a result of the processed glass body being used as the foreign matter. The "processed glass body" used herein indicates glass powder, glass beads, or the like. In order to reduce damage to erythrocytes (hemolysis) and breakage of devices used to prepare the serum according to the present invention, the shape of the processed glass body is preferably formed to be nearly spherical.

Furthermore, with the aim of rapid activation of factors to be activated such as platelets and coagulation factors, the surface of the processed glass body is preferably formed with a layer comprising a silicon dioxide compound. Examples of the silicon dioxide compound which may be used include at least one selected from glass, silica, diatomaceous earth, kaolin and the like, but are not limited thereto.

In a sixth aspect of the present invention, the human serum for cell culture according to the fifth aspect, the processed glass body is comprised of glass beads.

According to the sixth aspect of the present invention describes, the platelets in the fluid can be further activated, due the processed glass body being comprised of glass beads. Among them, porous glass beads are more preferable because they have a large contact area with the fluid. Furthermore, the surface area of the glass beads per 1 ml of the fluid is preferably in the range of 0.1 to 25($mm^2$/ml).

In a seventh aspect of the present invention, the human serum for cell culture according to any one of the first to sixth aspects, the human serum is prepared without being exposed to the atmosphere.

According to the seventh aspect of the present invention, the risk of contamination by bacteria, microorganisms, or the like can be reduced, resulting from the human serum being prepared without being exposed to the atmosphere. Accordingly, a serum of high safety can be produced in large quantities, thereby ensuring high safety. Furthermore, the human serum for cell culture according to the present invention is preferably prepared by such an apparatus, which will prevent it from being exposed to the atmosphere.

In an eighth aspect of the present invention, the human serum for cell culture according to any one of the first to seventh aspects, the human serum is usable for a regenerative medicine method.

According to the eighth aspect of the present invention, use of the serum as a medium for cell culture upon culturing by inoculating stem cells collected from a subject to this medium can culture the cells faster. Furthermore, because of the fact that the cells can be cultured using an autologous serum, the probability of adverse reaction or the like will be reduced, thereby being superior in safety.

Effects of the Invention

As can be appreciated from the foregoing description, it is to be understood that the human serum for cell culture according to the present invention contains a large amount of a growth factor, and accordingly, can more efficiently culture stem cells in comparison with a conventional serum. Accordingly, the use of this human serum for regenerative medicine ensures that tissues and functions of the subject can be regenerated safely and certainly.

PREFERRED MODE FOR CARRYING OUT THE INVENTION

The present invention is described in detail below.

A human serum for cell culture according to the present invention is preferably prepared with a serum preparation apparatus for a cell culture for preparing a serum for a cell culturing method that includes a serum preparing step of preparing a serum containing a cell growth factor and a culturing step of culturing cells in the presence of the prepared serum.

It is preferable that the serum preparation apparatus is usable for cell culture, and includes a blood reservoir for holding a fluid including at least humoral components and platelets derived from the blood having blood coagulation factors, and the blood reservoir has a serum producing function which produces a serum suitable for a cell culturing step. It is further preferable that the serum preparation apparatus is an apparatus of a closed system, which can produce a serum without being exposed thereof to the atmosphere. Here, the serum producing function is intended to indicate a function of activating the platelets in the fluids, and accordingly, increasing the content of the growth factors in a serum so that the recovery of the serum is facilitated. This function is provided by a blood coagulation accelerating solid whose specific gravity is greater than that of the fluids.

More specifically, it is preferable that the serum is prepared with the serum preparation apparatus described below, but this is not limited thereto.

Serum Preparation Apparatus

Figure 1:
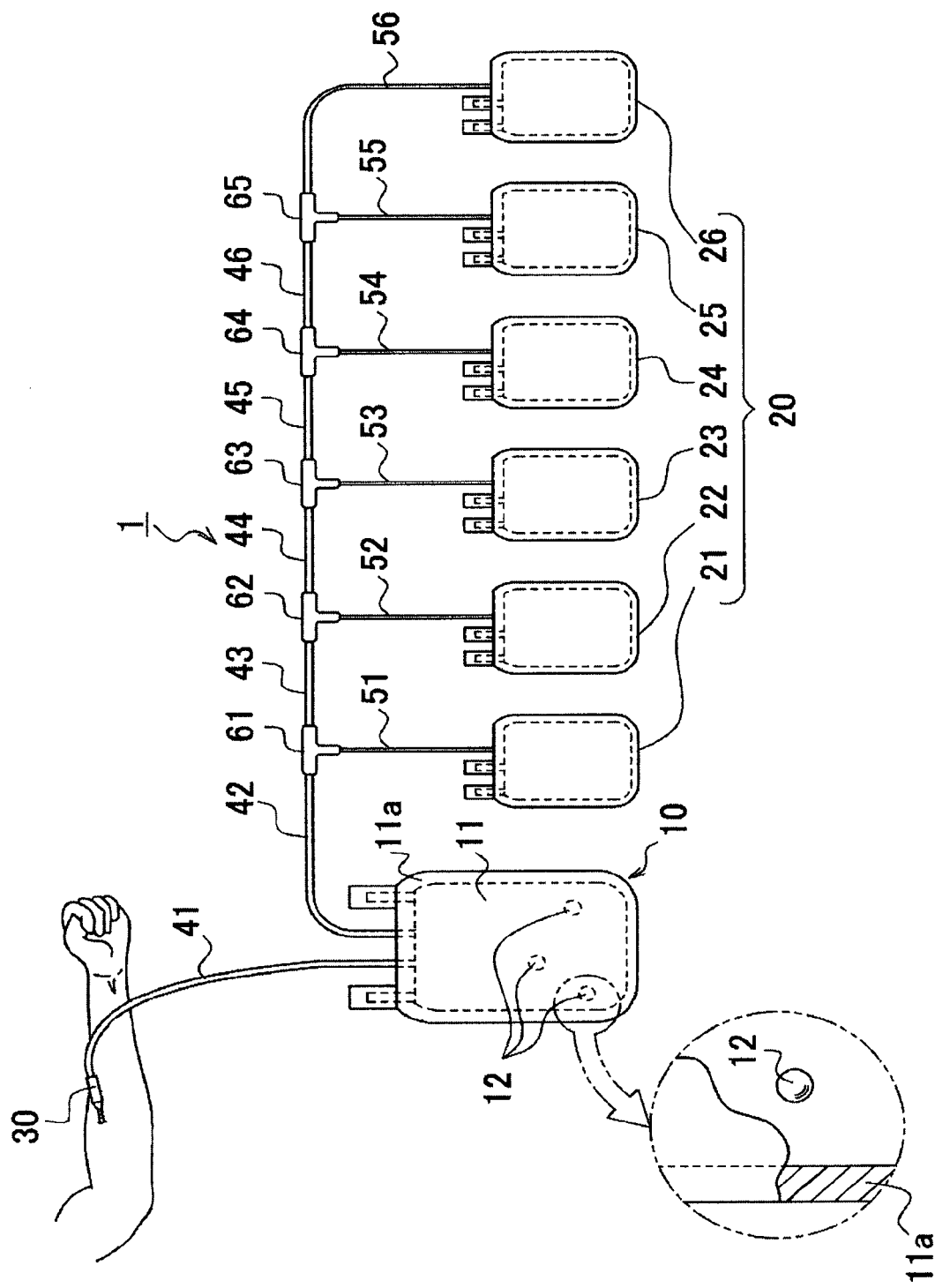
FIG. 1 illustrates a view of a serum preparation apparatus for preparing a human serum for cell culture according to the present invention.

As shown in FIG. 1, the serum preparation apparatus 1 comprises a blood reservoir 10, and a component storage member 20 as main elements. Among these, the blood reservoir 10 and the component storage member 20 are constituted from a main body part 11 formed with two sheets of a flexible resin material, for example, soft polyvinylchloride, fused to each other at the external marginal part 11a to give a bag shape, and a processed glass body 12 disposed inside of the main body part 11.

The glass processed bodies 12, serving as a blood coagulation accelerating solid in the main body part 11, is freely-movable in the main body part 11, each of the glass processed bodies 12 having a substantially spherical shape composed of, for example, soda glass. It is preferred to define the surface area of the processed glass body 12 to satisfy a relationship to the volume of reservable blood to be at least 0.1 mm$^2$/ml, so that activation of platelets and coagulation factors in the blood is promoted.

In connection with the blood coagulation accelerating solids in the blood reservoir, both a suspension of hemolysis and activation promotion of platelets and coagulation factors during the activation promoting step, and the centrifugal separation step are made possible when the surface area of the processed glass body 12 is defined to satisfy the relationship of 0.1 mm$^2$/ml to 25 mm$^2$/ml in the volume of the blood which can be reserved in the blood reservoir.

Two tubes 41 and 42 are connected in an air-tight manner at the upper edge end of the main body part 11 of the blood reservoir 10 to the connection ports thereof, respectively. The tube 41 among them serves as an introducing path for introducing the blood, and accordingly, a needle for collecting blood 30 or a junction, which can be connected to a needle for collecting blood, is connected at the other end thereof. The serum preparation apparatus thus constructed enables for the serum to be prepared from the collected blood without atmospheric exposure.

The other tube 42 connected in an air-tight manner to the blood reservoir 10 is connected to each of the bags 21 to 26 via tubes 43 to 46 and 51 to 56, and Branches 61 to 65. These serve as a discharging path for discharging separated blood components. These tubes 41 to 46 and 51 to 56 are constituted from a resin material having flexibility, for example, a material such as soft polyvinylchloride or the like. In this configuration, the bags 21 to 26 and each tube 51 to 56 of the component storage member 20 are also connected in an air-tight manner by, for example, solvent adhesion, thermal welding, ultrasound welding or the like.

Serum Preparation Step

The serum preparation step using the serum preparation apparatus 1 having the constitution as described above is explained with reference to FIG. 2 and FIG. 3.

Figure 2:
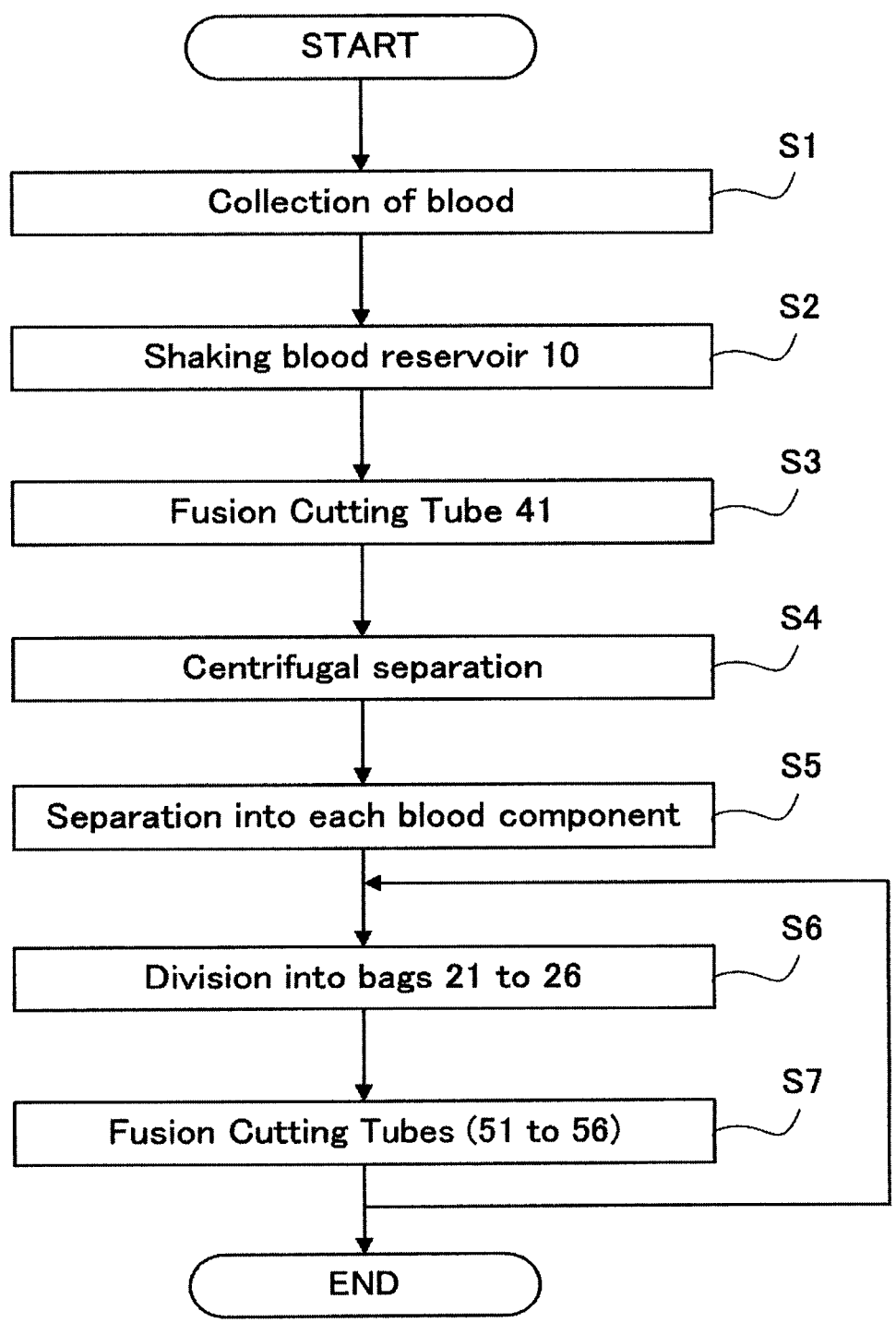
FIG. 2 illustrates a view of a procedure of preparing a human serum for cell culture according to the present invention.

As shown in FIG. 2, the blood separation process using the aforementioned serum preparation apparatus 1 is includes seven steps (S1 to S7) as generally classified.

First, in the first step of the process, the needle for collecting blood 30 shown in FIG. 1 is inserted into a subject (patient), and blood is collected. In this step, the blood collected from the needle for collecting blood 30 is stored in the blood reservoir 10, which is positioned lower, via the tube 41 (reservation step S1). Here, the channel of the tube 42 is closed on the blood reservoir 10 side by way of a clamp or the like such that the collected blood in the blood reservoir 10 does not flow into the component storage member 20. The reservation step S1 is terminated after the required amount has been collected, taking into account the patient's physical condition upon collecting the blood. The required amount referred to herein may be approximately 200 to 600 ml when the physical constitution and physical condition of the patient are problem free.

Figure 3:
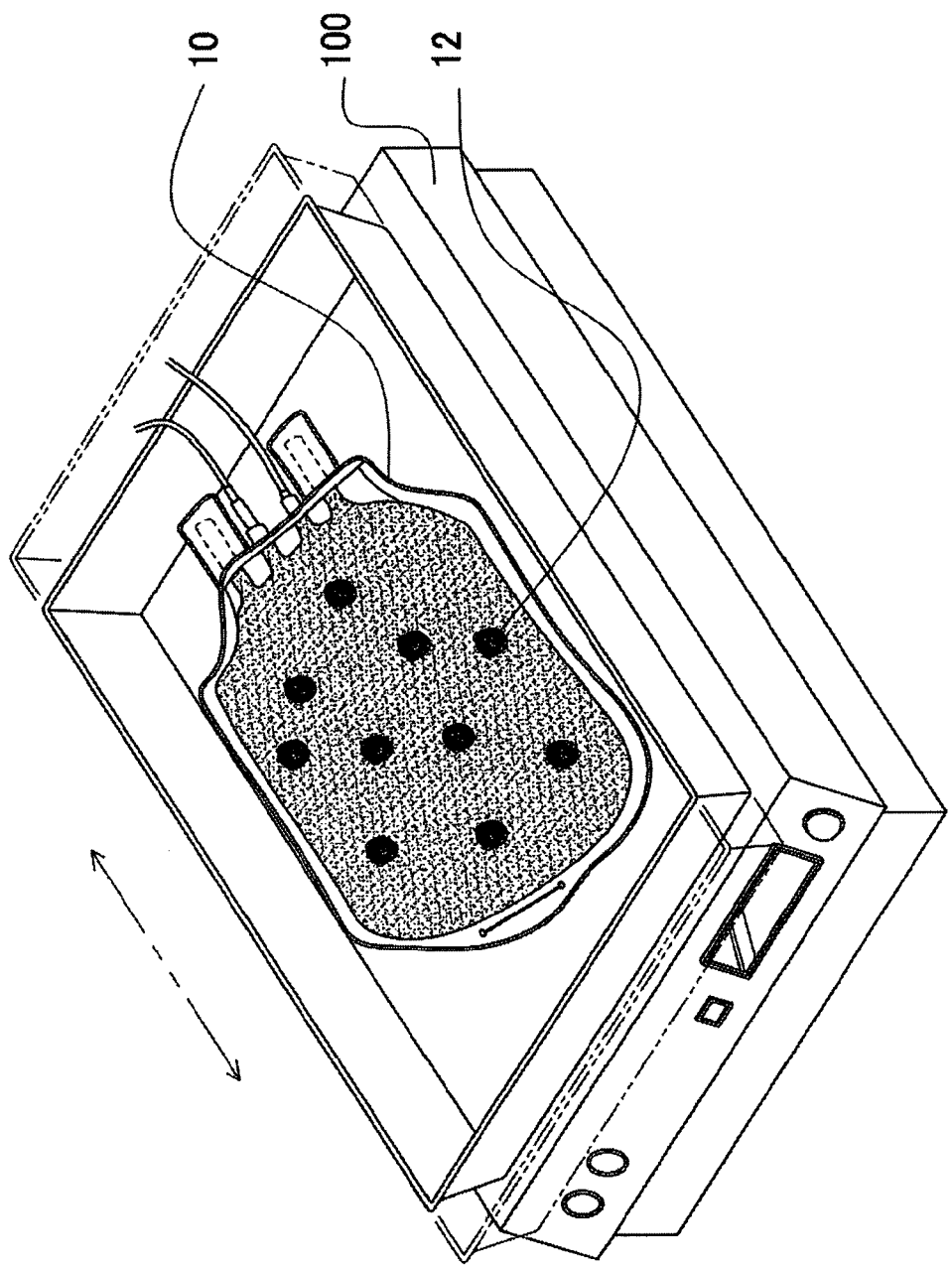
FIG. 3 illustrates a view of a state of shaking a blood reservoir 10 of the serum preparation apparatus according to the present invention.

Next, as shown in FIG. 2, after initiating the reservation step S1, the blood reservoir 10 is shaken (activation promoting step S2) while the reservation step S1 is being carried out. As shown in FIG. 3, the blood reservoir 10 storing the collected blood is gently agitated by a shaking apparatus 100 brought into contact with the glass processed bodies 12 stored inside. Then, the platelets and coagulation factors consisted in the blood are coagulated on the surface of the processed glass body 12, and from the platelets activated during the coagulation, growth factors derived therefrom are released. (Also, this activation promoting step carried out at a low temperature is effective in the acceleration of platelet agglutination.) Following the reservation step S1, the needle for collecting blood 30 is removed from the subject of the blood collection, and then a part of the tube 41 connecting the needle for collecting blood 30 with the blood reservoir 10 is cut and fused, sealing its cut edge (fusion cutting step S3) at the same time.

On the other hand, the blood reservoir 10 separated from the patient proceeds through the activation promoting step S2 together with the component storage member 20, and each of the tubes 42 to 46 and 51 to 56 connecting therebetween, as well as branches 61 to 65 and the like. They are bundled to be compact, and are subjected to a centrifuge separation (centrifugal separation step S4). Conditions for centrifugal separation of the blood reservoir 10 may be defined depending on the amount of the reserved blood and type of the components to be separated; however, they may be defined to be, for example, 2,250 g×10 min, at 4° C. The tube 42 is then maintained in the state with the channel being closed by a breakable partition wall or a clamp, similar to the case of the reservation step S1.

In cases where an anticoagulant is added previous to blood collection, the fusion cutting step S3 and the centrifugal separation step S4 may be carried out prior to the activation promoting step S2. In this instance, the centrifugal separation may be conducted under the following conditions:

centrifugal separation of whole blood: 4,400 g×4 to 6 min, 2,250 g×10 min; and centrifugal separation of platelet-rich plasma (PRP): 1,100 g×4 to 6 min.

Referring back to FIG. 2, the factors to be activated including hemocyte components, which were activated in the activation promoting step S2 through the centrifugal separation step S4, form a block shape and are separated from the blood (separation step S5). Furthermore, the serum 71 separated and extracted in the blood reservoir 10 in the separation step S5 is sequentially divided into all or some of the bags 21 to 26 by compressing the blood reservoir 10 (discharging step S6).

After the bag 21 is filled with a required amount of the serum, the tube 51 is cut and sealed (fusion cutting step S7). This cutting and sealing may be performed using a method that is similar to the cutting and sealing of the tube 42 prior to the aforementioned centrifugal separation step S4. Moreover, the bag 21 having the serum contained therein is subjected to a storage treatment such as frozen storage.

The discharging step S6 and fusion cutting step S7 are carried out sequentially on each of the bags 21 to 26, and the operation for serum preparation is stopped when the serum is contained in all or some of the bags 21 to 26. Additionally, the erythrocytes may be washed and diluted, as needed, with physiological saline, or an anticoagulant such as CPD, or ACD-A liquid, or a liquid for preserving blood such as MAP, and can be stored as blood for transfusion.

EXAMPLES

Hereinafter, the present invention is explained in more detail, but not in any way to limit the present invention to these Examples.

Example 1

Fresh human blood 20 (ml) was added to a vessel in which five glass beads (φ: 4 mm, 50 mm²) were stored, and shaken by a Multi Shaker (MMS-300, manufactured by Tokyo Rikakikai Co., Ltd.). At 10, 20, 30 and 60 minutes after shaking was initiated, 1 (ml) of blood was collected in a sampling tube in which an anticoagulant was stored, and the blood was centrifuged to isolate a serum. In addition, CPD-added blood was collected from the same subject to isolate plasma. Calcium chloride was added to the isolated plasma so that fibrin was deposited at 37° C. and a serum was prepared. The growth factors (PDGF-BB, TGF-β1) were measured for both the serum prepared from the vessel in which glass beads were stored, and the serum prepared from the CPD-added blood. The results are illustrated in Table 1. The amounts of the growth factors (TGF-β1, PDGF-BB) were measured by a commercially available test kit manufactured by R&D SYSTEMS, Inc. using a microplate reader (Multiskan BICHROMATIC manufactured by Labsystem).

TABLE 1

Differences in content of growth factors depending upon origins of the serum

| | Origin of Serum | | | | |
|---|---|---|---|---|---|
| | Derived from Vessel containing five Glass Beads Elapsed Time Following Shaking | | | | Derived from CPD-Added |
| | 10 minutes | 20 minutes | 30 minutes | 60 minutes | Plasma |
| PDGF-BB | 40.5 pg/mL | 753.7 pg/mL | 1677.2 pg/mL | 1677.2 pg/mL | <32.5 pg/mL |
| TGF-β1 | 21.2 ng/mL | 24.4 ng/mL | 26.4 ng/mL | 29.6 ng/mL | 1.5 ng/mL |

As for PDGF-BB, in the serum prepared from the vessel in which five glass beads were contained, the content of PDGF-BB increased as time elapsed following the shaking, and 1677.2 (pg) of PDGF-BB was released per 1 ml of the serum after 60 minutes elapsed. In the serum prepared from the plasma of the same subject, the amount of PDGF-BB then was less than 32.5 (pg/ml) of the detection limit. As for TGF-β1, in the serum prepared from the vessel in which five glass beads were contained, 21.2 (ng) of TGF-β1 had already been released per 1 (ml) after 10 minutes of shaking. The amount released thereafter gradually increased in a time dependent manner, and 29.6 (ng) of TGF-β1 was released after 60 minutes. On the other hand, in the serum prepared from the plasma of the same subject, the amount of TGF-β1 was 1.5 (ng) per 1 (ml) of the serum.

Example 2

The following three types of vessels for collecting blood were prepared. The first type of vessel for collecting blood (specimen 3) contained no glass beads therein, the second type of vessel for collecting blood (specimen 1) contained five glass beads therein, and the third type of vessel for collecting blood (specimen 2) contained 20 polyethylene pellets therein. 20 ml of fresh blood derived from the same subject was added to each of the vessels, and was shaken by a Multi Shaker (MMS-300, manufactured by Tokyo Rikakikai Co., Ltd.). At 10, 20, 30 and 60 minutes after shaking was initiated, 1 (ml) of each blood was collected in a sampling tube containing an anticoagulant, and the number of platelets was counted using a hemocryte counting apparatus (Multiparameter automated hematology analyzer K-4500 manufactured by SYSMEX CORPORATION).

Furthermore, each of the specimens was centrifuged to isolate a serum, and the growth factors (PDGF-BB, TGF-β1) were measured for the serum. The amounts of the growth factors (TGF-β1, PDGF-BB) were measured by way of a commercially available test kit manufactured by R&D SYSTEMS, Inc. using a microplate reader (Multiskan BICHROMATIC manufactured by Labsystem).

Moreover, blood was collected from the same subject into a commercially available vacuum blood collection tube (VENOJECT II manufactured by TERUMO CORPORATION) designed for a clinical laboratory, and the collected blood was allowed to stand at room temperature for approximately one hour, followed by isolation of a serum; the growth factors were measured in the same manner. The number of platelets is represented by a residual ratio of the number of platelets to the number of platelets immediately after blood collection, which is assumed to be 100%. The amount of each of the cell growth factors contained in a serum prepared from a vacuum collection tube is assumed to be a potential amount of each of the growth factors contained in the platelets. The amount of each of the growth factors is represented by a release ratio of an amount of each of the cell growth factors of a serum obtained in a period of elapsed time following the shaking to the potential amount of each of the cell growth factors.

Number of Platelets

Figure 4:
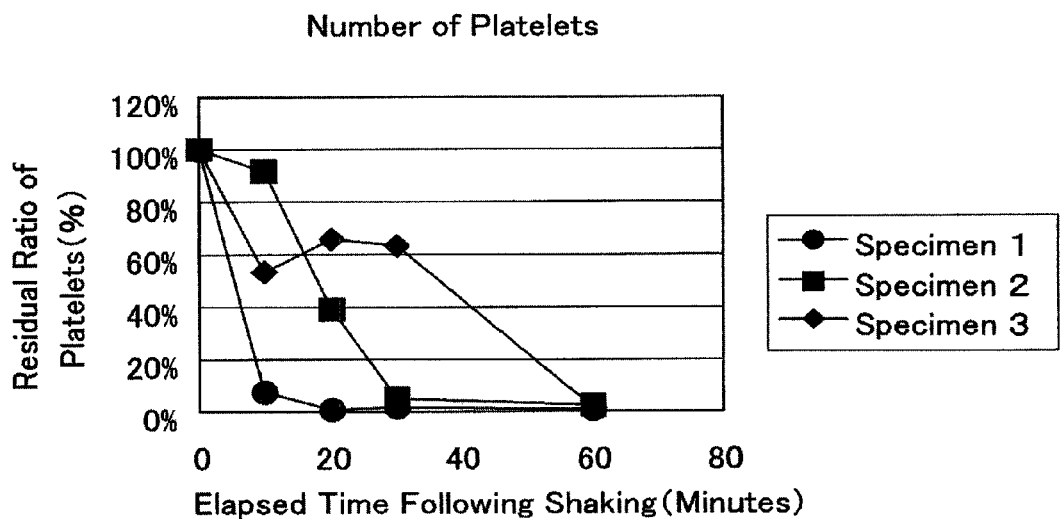
FIG. 4 illustrates a graph of a relationship between elapsed time following the shaking and the residual ratio of platelets in each specimen.

FIG. 4 illustrates a graph of a relationship between elapsed time following the shaking and the residual ratio of platelets in each specimen. The residual ratio of platelets in specimen 1 was reduced to approximately 2% within 20 minutes after shaking had been initiated. The residual ratio of platelets in specimen 2, on the other hand, was reduced within 30 minutes after shaking had been initiated, slightly behind specimen 1. Furthermore, it has been revealed that the residual ratio of platelets in specimen 3 was reduced to less than 2% in 60 minutes after shaking had been initiated, although it was rapidly reduced immediately after shaking had been initiated.

Release Ratio of PDGF-BB

Figure 5:
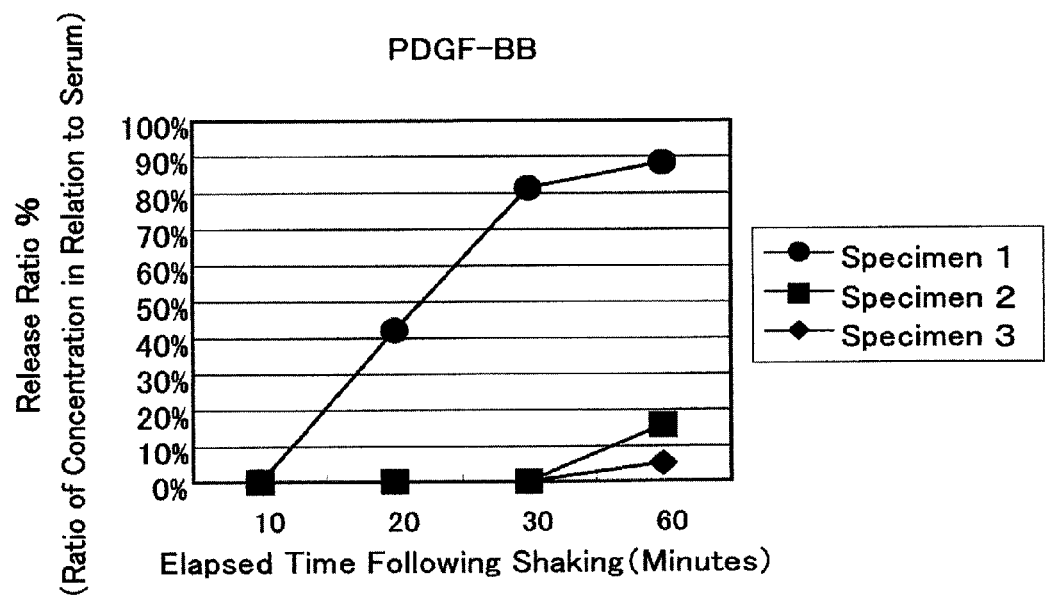
FIG. 5 illustrates a graph of a relationship between elapsed time following the shaking and the release ratio of PDGF-BB.

FIG. 5 illustrates a graph of a relationship between elapsed time following the shaking and the release ratio of PDGF-BB in each of the specimens. It has been discovered that, as for specimen 1, PDGF-BB was rapidly released in a time dependent manner, so that 90% of the potential amount in the serum was released within an hour after the shaking. As for the other two specimens, less than 20% of the amount of PDGF-BB to the potential amount in the serum was released, although the number of platelets had been reduced.

Release Ratio of TGF-β1

Figure 6:
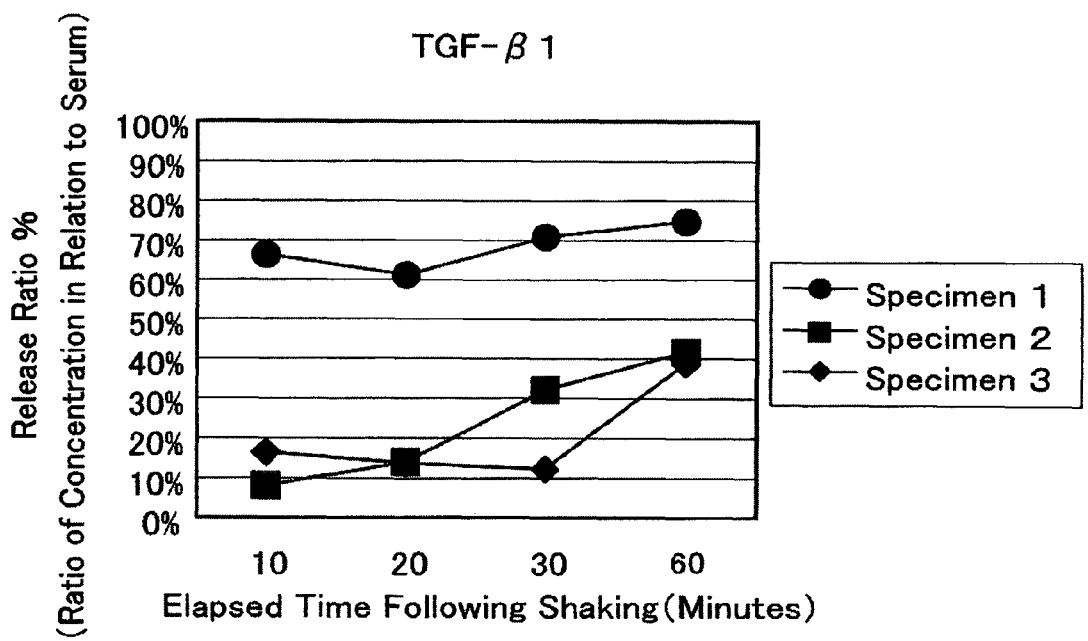
FIG. 6 illustrates a graph of a relationship between elapsed time following the shaking and release ratio of TGF-β1.

FIG. 6 illustrates a graph of a relationship between elapsed time following the shaking and the release ratio of TGF-β1 in each of the specimens. As for the serum in specimen 1, nearly 70% of the amount of TGF-β1 to the potential amount in the serum was released within ten minutes after the shaking. As for the other two specimens, although it has been found that the amount of the release was increased, the release ratio of the amount of TGF-β1 to the potential amount in the serum had remained approximately 40% within sixty minutes after the shaking. As can be seen from the aforementioned results, it has been revealed that the polyethylene pellet plays a role similar to the glass beads in terms of eliminating the platelets in the blood, but cannot activate the platelets.

The invention claimed is:

1. A method of producing human serum for cell culture, the method comprising:
    receiving and storing blood from a donor in a blood reservoir containing a blood coagulation accelerating substance having a surface area of 0.1 to 25 mm$^2$ per ml of said blood, said blood reservoir formed of a resin material having flexibility to give a bag shape;
    a process of activating platelets in the blood by shaking the blood reservoir, for contacting the blood and the blood coagulation accelerating substance, to emit cell growth factors from the blood platelets into the blood;
    a centrifugation process of separating serum including cell growth factors from the blood, by centrifugation of the blood reservoir containing the blood with a component storage part bundled with the blood reservoir, after the process of emitting the cell growth factors into the blood; and
    a process of transferring the serum to the component storage part via a tube that is connected in an airtight manner with the blood reservoir and is formed of a resin material that has flexibility by compressing the blood reservoir, after the process of separating the serum including the cell growth factors.

2. A method of producing human serum for cell culture according to claim 1, wherein the blood coagulation accelerating substance is glass beads.

3. A method of producing human serum for cell culture according to claim 2, wherein a layer formed from a silicon dioxide compound is formed on a surface of the glass beads, and the silicon dioxide compound is at least one selected from glass, silica, diatomaceous earth, and kaolin.

4. A method of producing human serum for cell culture according to claim 2, wherein the shape of the glass beads is substantially spherical.

5. A method of producing human serum for cell culture according to claim 3, wherein the shape of the glass beads is substantially spherical.

* * * * *